United States Patent
Stephens

(10) Patent No.: US 10,968,194 B2
(45) Date of Patent: Apr. 6, 2021

(54) EQUIPMENT AND METHOD FOR CONTINUOUSLY PROCESSING PLANT MATERIAL

(71) Applicant: Delta Separations LLC, Cotati, CA (US)

(72) Inventor: Benjamin K. Stephens, Santa Rosa, CA (US)

(73) Assignee: DELTA SEPARATIONS, LLC, Cotati, CA (US)

( * ) Notice: Subject to any disclaimer, the term of this patent is extended or adjusted under 35 U.S.C. 154(b) by 0 days.

(21) Appl. No.: 16/833,573

(22) Filed: Mar. 28, 2020

(65) Prior Publication Data

US 2020/0308133 A1 Oct. 1, 2020

Related U.S. Application Data

(60) Provisional application No. 62/825,180, filed on Mar. 28, 2019.

(51) Int. Cl.
| | |
|---|---|
| *B01D 11/02* | (2006.01) |
| *C07C 37/68* | (2006.01) |
| *B01D 21/00* | (2006.01) |
| *C07D 311/78* | (2006.01) |

(52) U.S. Cl.
CPC ........ *C07D 311/78* (2013.01); *B01D 11/0257* (2013.01); *B01D 11/0288* (2013.01); *B01D 21/0012* (2013.01); *C07C 37/685* (2013.01); *B01J 2219/00164* (2013.01)

(58) Field of Classification Search
CPC ........... B01D 11/0257; B01D 11/0288; B01D 21/0012
See application file for complete search history.

(56) References Cited

U.S. PATENT DOCUMENTS

| | | |
|---|---|---|
| 2003/0017106 A1 | 1/2003 | Abercrombie |
| 2012/0237983 A1 | 9/2012 | Harlick |
| 2015/0258153 A1 | 9/2015 | Rosenblatt et al. |

(Continued)

FOREIGN PATENT DOCUMENTS

| | | |
|---|---|---|
| EP | 3453397 A1 | 3/2019 |
| GB | 2459125 A | 10/2009 |
| WO | 8604938 A1 | 8/1986 |

OTHER PUBLICATIONS

International Searching Authority, "Notification of Transmittal of the International Search Report and the Written Opinion of the International Search Authority" dated May 27, 2020, in International Application No. PCT/US20/25582, nine pages.

*Primary Examiner* — Bradley R Spies
(74) *Attorney, Agent, or Firm* — Dickinson Wright PLLC

(57) ABSTRACT

Cannabinoids can be separated or extracted from plant material. Versions can include a process for separating trichomes from plant material, including mixing plant material with a fluid in a metered feed system and forming a slurry; pumping the slurry into a turbulent processor, agitating the slurry between rotating and static teeth and shearing trichomes from the plant material to form a mixture of fluid, trichomes and plant material; coarse filtering the mixture and removing portions of the plant material to form an interim mixture; and then second filtering the interim mixture and removing other plant material and some trichomes to form a resulting mixture comprising other trichomes and fluid.

19 Claims, 7 Drawing Sheets

(56) References Cited

U.S. PATENT DOCUMENTS

2017/0319009 A1* 11/2017 Seckel ................ B02C 18/2216
2017/0335512 A1    11/2017 Mohammadi et al.
2019/0039074 A1*  2/2019 Rose ....................... B05B 13/04
2019/0241536 A1*  8/2019 Durkacz ............... C07C 37/004

* cited by examiner

EQUIPMENT AND METHOD FOR CONTINUOUSLY PROCESSING PLANT MATERIAL

CROSS-REFERENCE TO RELATED APPLICATION

This application claims priority to and the benefit of U.S. Prov. Pat. App. No. 62/825,180, filed Mar. 28, 2019, and is incorporated herein by reference in its entirety.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISC APPENDIX

Not Applicable.

BACKGROUND

1. Field of the Disclosure

The present disclosure relates generally to processing plant material. More specifically, the present disclosure relates to a continuous system and method of separating or extracting cannabinoids from cannabis plants.

2. Description of the Related Art

Hashish is a consumable compress of purified cannabinoid resins from the glandular trichomes of the cannabis plant. The trichomes are found on the flowers, and to a lesser extent, in the stems and leaves of the plant. Historically, separating the cannabinoids from the plant has been very difficult as the cannabinoid resin is quite sticky. Methods such as flat screening or dry sieving require practice and skill, are inefficient, and often result in a lower quality product that contains broken leaf-matter contaminants. Machines that tumble the plant flowers and collect the sticky cannabinoids on sieving screens, although inexpensive, are also inefficient, and are difficult to clean and reuse.

Some success has been found with a washing process using ice, water, and a mechanical agitator. The ice cools the resinous trichome heads, making them more brittle and reducing their stickiness. Mechanical agitation forces the trichome heads to break away from their stalks and botanical material. These processes not only use excessive energy due to the requirement for ice and continual cooling, but are also quite labor intensive and inefficient, generally yielding only 30% to 50% of the potential cannabinoid material, even after multiple washings. Some additional success has been found using solvents to dissolve the plant biomass material, leaving the cannabinoids with the solvent in a tincture form. Basic washing machines that use solvents, however, take time for the solvents to work and can introduce harsh flavors to the end product due to the long duration of blending and agitating. Although these solutions are workable, improvements in cannabis processing continue to be of interest.

SUMMARY OF THE DISCLOSURE

Embodiments of a system, method and apparatus for processing plant material are disclosed. For example, cannabinoids can be separated or extracted from plant material. Versions can include a process for separating trichomes from plant material, including mixing plant material with a fluid in a metered feed system and forming a slurry; pumping the slurry into a turbulent processor, agitating the slurry between rotating and static teeth and shearing trichomes from the plant material to form a mixture of fluid, trichomes and plant material; coarse filtering the mixture and removing portions of the plant material to form an interim mixture; and then second filtering the interim mixture and removing other plant material and some trichomes to form a resulting mixture comprising other trichomes and fluid.

In an alternate embodiment, cannabinoids can be extracted from plant material by mixing plant material with a solvent in a hopper and forming a slurry; pumping the slurry into a turbulent processor, agitating the slurry and extracting cannabinoids from the plant material and forming a mixture of solvent with plant material and dissolved cannabinoids; coarse filtering the mixture and removing portions of the plant material to form an interim mixture of solvent, other plant material and dissolved cannabinoids; second filtering the interim mixture and removing the other plant material to form a resulting solution comprising substantially only the solvent and dissolved cannabinoids; and then processing the resulting solution to remove the dissolved cannabinoids from the solvent.

BRIEF DESCRIPTION OF THE DRAWINGS

A more complete understanding of the present disclosure may be derived by referring to the detailed description and claims when considered in connection with the figures, wherein like reference numbers refer to similar items throughout the figures.

DETAILED DESCRIPTION OF THE DISCLOSURE

Figure 1:
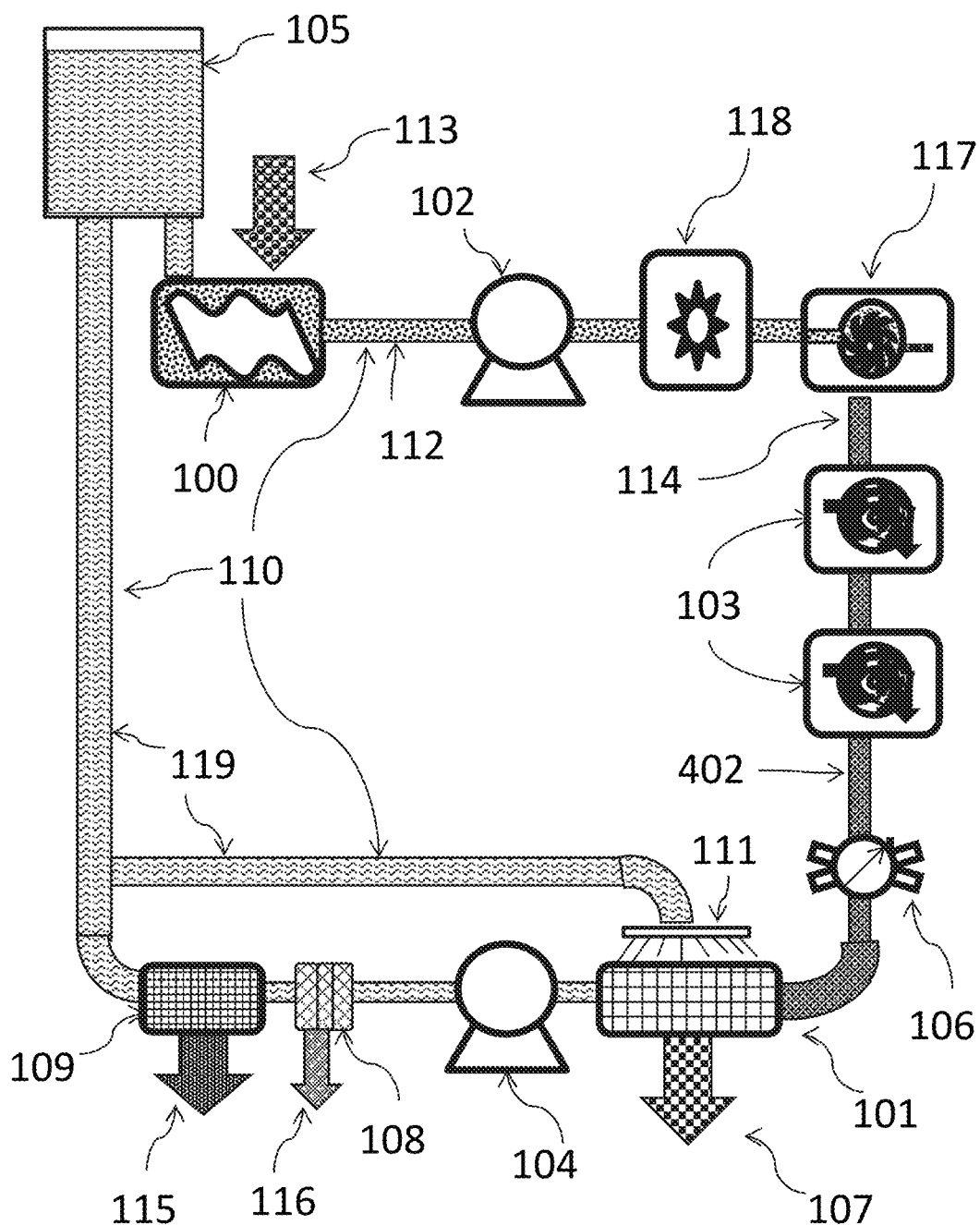
FIG. 1 is a schematic diagram of an embodiment of the equipment for the overall process when using water as the fluid.

In the following detailed description, reference is made to the accompanying drawings which form a part of the disclosure and, which show by way of illustration, and not of limitation, specific embodiments by which the disclosure may be practiced. The drawings, the foregoing discussion, and the following description are exemplary and explanatory only, and are not intended to limit the scope of the disclosure or its application in any manner.

Embodiments can optionally include one or more of a feed device 100, first pump 102, liquid ring pump 117, shear blender 103, diaphragm valve 106, coarse filter 101, positive displacement pump (PDP) 104, filter pack 108, fine filter 109, spray bar 111 and holding tank 105. In one example, the feed device 100 can comprise a Screw Sump for a Waukesha 130 Pump, by Carlsen and Associates of Healdsburg, Calif. Another example of the feed device 100 can be an Aqseptence Group Noggerath Grit Classifier GS. An example of the first pump 102 can comprise a Positive Displacement Lobe Pump, by SPX Flow, model Waukesha 130 Pump. Another example of the first pump 102 can be a Netzsch Pumps model Progressive Cavity Pump—Nemo Bmax Mixing Pump. An example of the liquid ring pump 117 can comprise a Fristam Pumps model FZX 2100 Liquid Ring Pump. An example of the shear blender 103 can comprise a Fristam Pumps model FS 352 Shear Blender. One example of the diaphragm valve 106 can comprise a Glacier Tanks Diaphragm Valve. An example of the coarse filter 101 can be a Vincent Corporation model VDS-36 Side Hill Screen, and it can be a parabolic screen. An example of the PDP 104 can be a Pacer Pumps model PC Centrifugal Pump. Examples of the filter pack 108 and fine filter 109 can be a Spiral Water Technologies model Self Cleaning Mechanical Separator S1000. Versions of the holding tank 105 can contain fluid or be connected to an external fluid source, which can be connected with stainless steel, plastic or other suitable pipes 110 and/or tank, such as a stainless steel tank.

In some versions, the process can begin by placing bulk cannabis plants 113 into the feed device 100 and adding water from the holding tank 105 to form a slurry 112. The bulk cannabis plants 113 can be milled or ground to a desired size, such as approximately 1/32, 1/4, 3/8 or 1/2 inch size. Such small sizes can reduce the risk of clogging the system during processing. If the bulk cannabis plants 113 are not pre-milled, an optional grinder 118 can be added to the system, such as shown in FIG. 1, to reduce the particulate size of the bulk cannabis plants 113. In an example, the grinder 118 can comprise a JWC Environmental model Muffin Monster Inline Sewage Grinder. In one version, the feed device 100 can be a one or two-step auger system with a metered feed that gently blends the bulk cannabis plants 113 with the fluid and moves the slurry 112 at, for example, a constant rate toward the first pump 102.

Embodiments of the first pump 102 can be a positive displacement lobe pump. However, any type of pump suitable for moving high solid fluids may be used, such as a sinusoidal, progressive cavity or a hose (peristaltic) pump. The first pump 102 can move the slurry 112 through the system to the (optional) grinder 118, or directly to the liquid ring pump 117. Versions of the liquid ring pump 117 can be a commercially available liquid ring pump. However, any type of apparatus configured to enable a shear mixing environment may be used. In one example, the liquid ring pump 117 can serve to remove trichomes from the plant material through its highly turbulent internal mechanism, rather than to merely serve as a pump to move material through the process. The high solids mixture 114 from the liquid ring pump 117 can be a mixture of separated trichomes, larger plant material, smaller plant material and fluid, for example.

Figure 3:
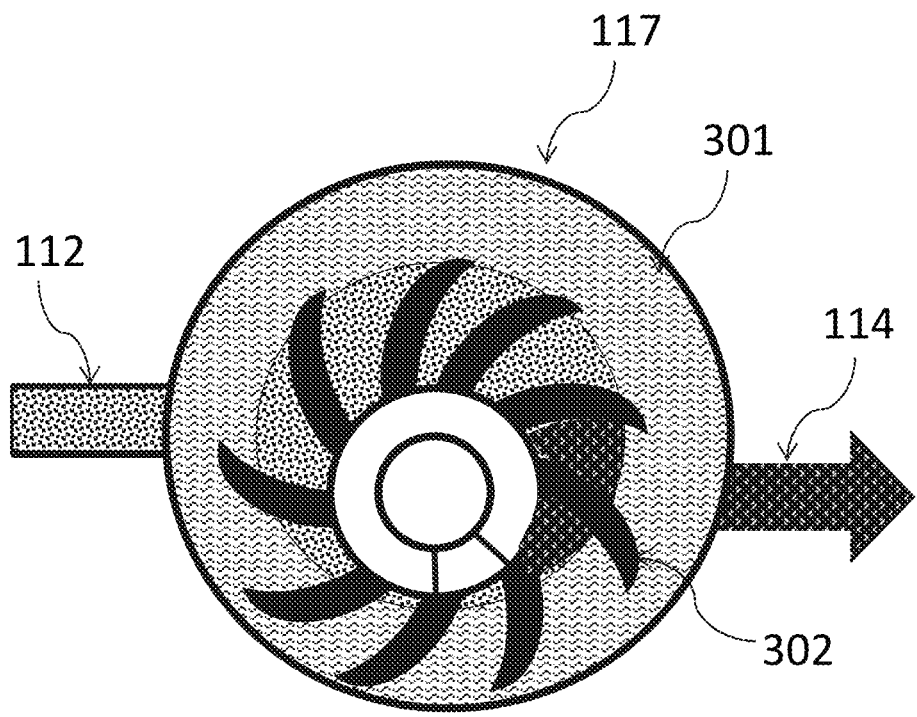
FIG. 3 is a schematic diagram depicting an embodiment of the passage of material through a liquid ring pump.

As shown in FIG. 3, embodiments of the liquid ring pump 117 can draw in the slurry 112 and circulate it as a high solids mixture 114. In one embodiment, the pump can be a liquid ring pump having a spinning off-center blade ring 302, in conjunction with a water ring 301, that can pull the slurry 112 into the pump 102 and circulate the high solids mixture 114.

Figure 5:
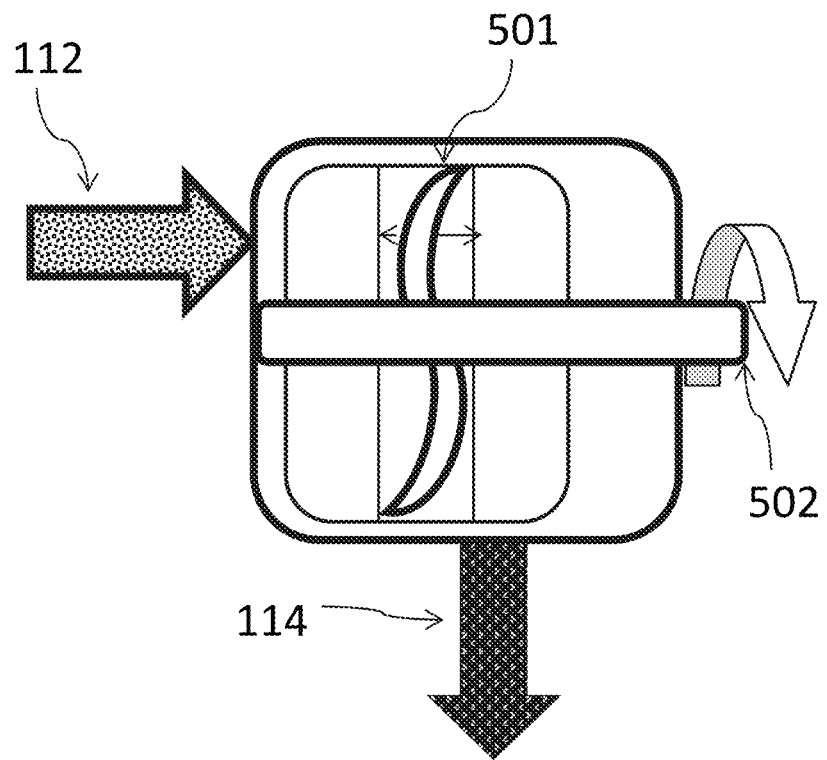
FIG. 5 is a schematic diagram depicting an embodiment of the passage of material through a sinusoidal pump.

Alternatives to the liquid ring pump can include any commercially available pump, such as a self-priming pump. For example, if a sinusoidal pump is used, it can have a single sinusoidal rotor 501 (FIG. 5) and a number of chambers, such as four evenly-sized chambers, with a rotor 501 that is rotated on a shaft 502. The slurry 112 can be pulled through the inlet into each chamber in sequence. As the chamber rotates, it contracts the space, closes and then discharges the high solids mixture or mixture 114 to the outlet port.

Figure 4:
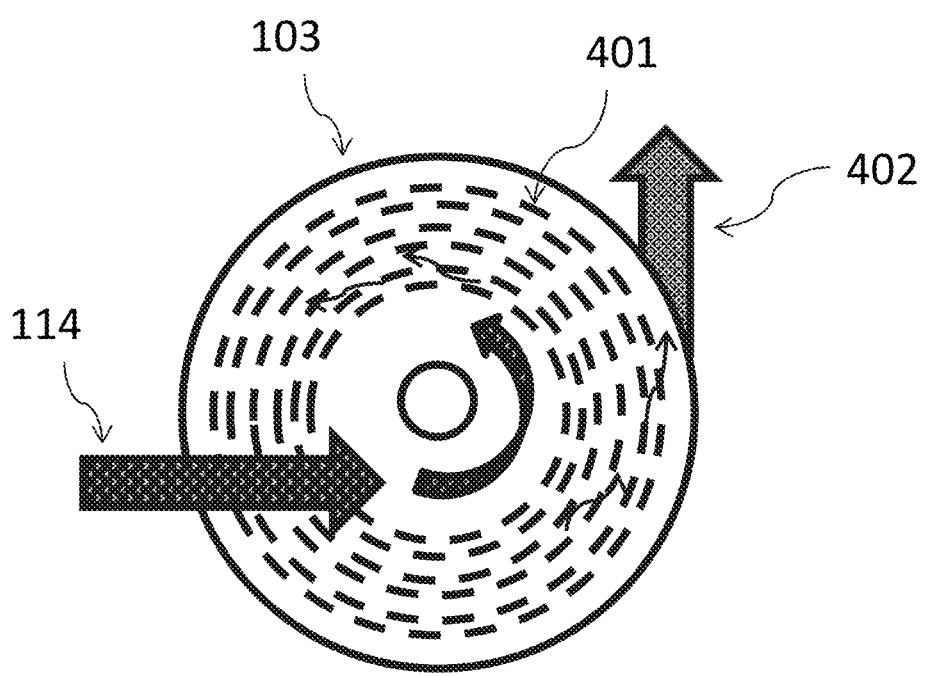
FIG. 4 is a schematic diagram of an embodiment of the interior of a shear blender depicting the flow of the high solids plant material through the static and rotating teeth.

In some embodiments, the high solids mixture 114 from the liquid ring pump 117 can be transported, such as by pipe, into (e.g., the center) of the shear blender 103. The shear blender 103 can comprise alternating rings of static and rotating teeth 401, in some examples. The rotating teeth 401 can be configured to rotate in a range of approximately 5 to 60 hz, but higher frequencies can be used to achieve additional turbulence. The clearance between the teeth can be prescribed, such as approximately 0.5 millimeters. The clearance can be in a range of about 0.1 mm to about 1 mm, or more, depending on the application. The high solids mixture 114 can be drawn outward between the static and rotating teeth 401 as shown in FIG. 4, macerating the cannabis flowers, stems and leaves.

Because the trichomes are so small, and the flow is so fast, the trichomes can be sheared off the cannabis material and pass through the teeth without damage. The smaller solids effluent 402 from the shear blender 103 can be a mixture of liquid with smaller botanical material 107, trichomes 115 and, for example, trichomes and macerated botanical material 116. Optionally, the smaller solids effluent 402 may be fed into one or more additional shear blenders 103 to further remove trichomes from the botanical material. An optional diaphragm valve 106 (FIG. 1) may be used, e.g., downstream, of the shear blender(s) 103 to create back pressure in the system to slow the progress of material through the shear blender(s) 103.

Figure 6:
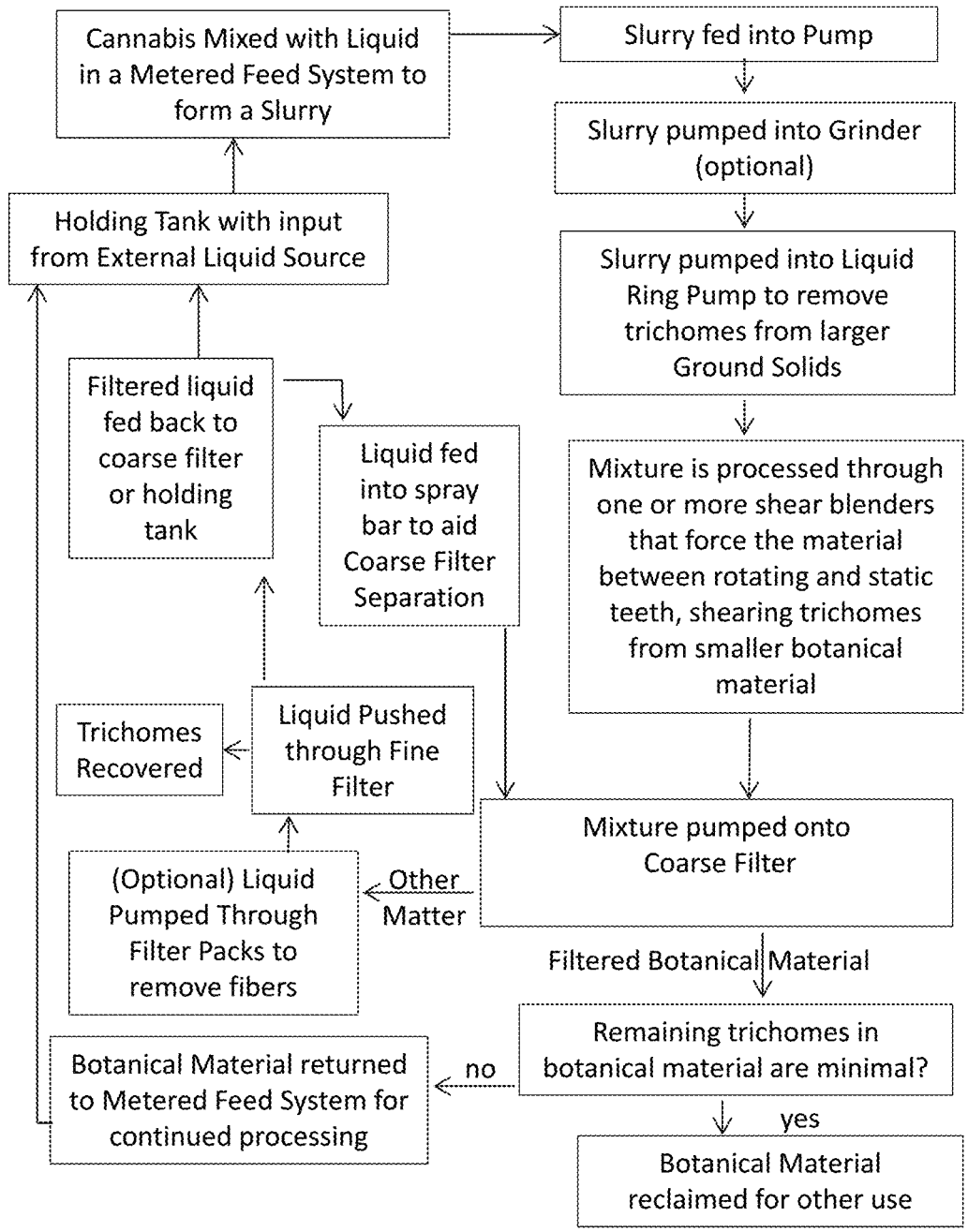
FIG. 6 is a flowchart of an embodiment that uses water as the liquid.
Figure 7:
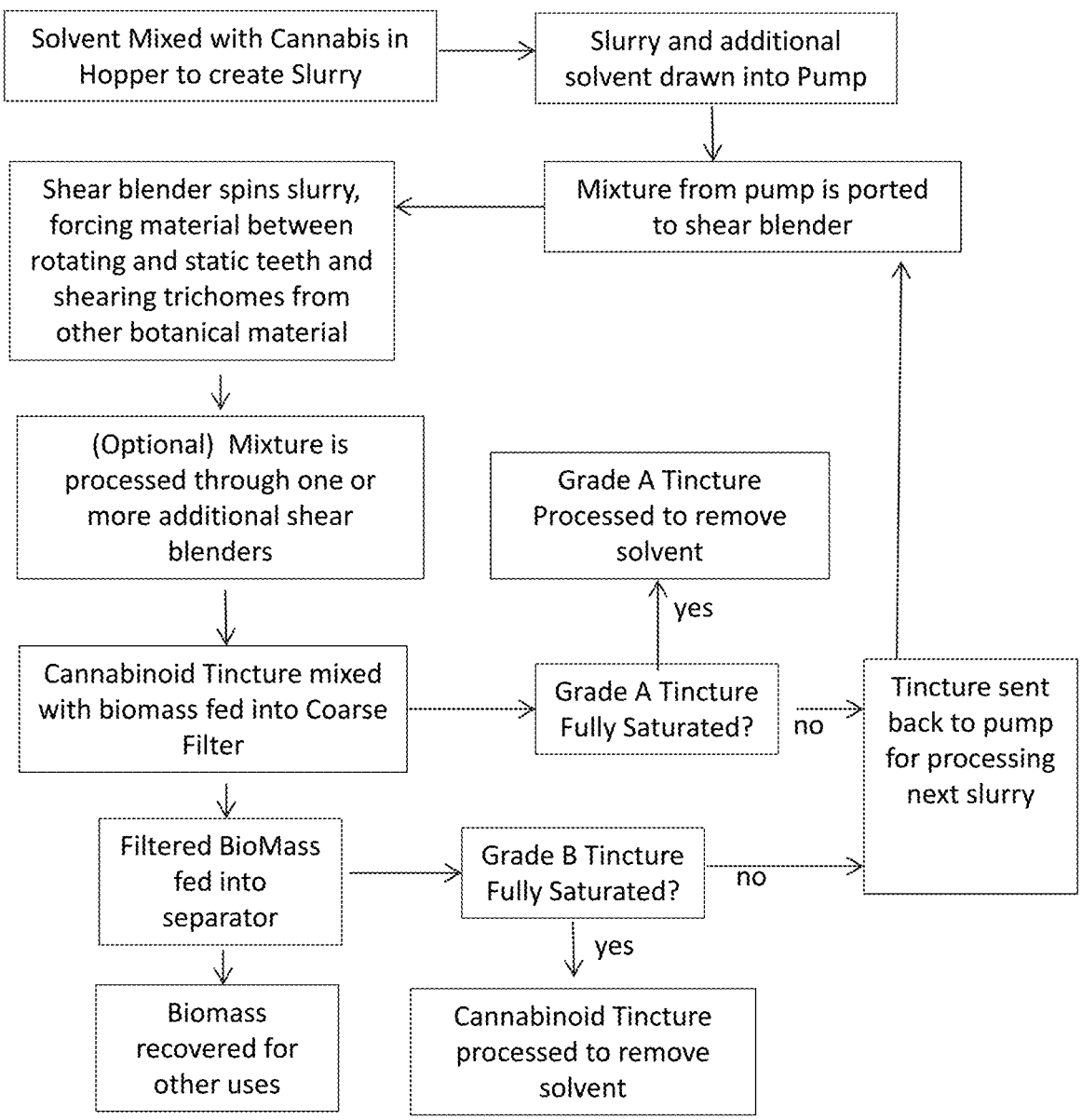
FIG. 7 is a flow chart of an embodiment that uses an alternate solvent.

Versions of the smaller solids effluent 402 from the shear blender(s) 103 can be fed into a coarse filter 101. The course filter 101 can be a drum screen. However, the coarse filter also can be a hydrostatic screen, fiber filter, other coarse filtering device, or a combination thereof. Embodiments of the size for filtration of the coarse filter 101 can be 190 microns or more, 220 microns or more, in a range of about 190 to about 225 microns, or a range of about 190 microns to about 500 microns. To aid in processing the smaller solids effluent 402 through the coarse filter 101, and to assist with removing the sticky trichomes from the solids, a high pressure spray of filtered liquid 119 from the output of the downstream fine filter 109 may be ported back to a spray bar 111 and sprayed on the screen. The coarse filter 101 separates out the larger botanical material 107, which can be ported back to the feed device 100 for repeated processing if it still contains trichomes, as indicated in the flow chart shown in FIG. 6. If the majority of cannabinoids have been removed, the larger botanical material 107 may be discarded or further processed for secondary hemp usage such as feed for livestock.

In some examples, a positive displacement pump 104 can be used to pull the remaining material through the coarse filter 101 and send it downstream to a fine filter 109. An optional medium filter 108 may be used before the fine filter 109. For example, the medium filter 108 can be used to collect at least some of the trichomes, and/or help remove some of the trichomes and any fibers 116 or other particulate matter that were not captured by the coarse filter 101. The medium filter 108 can be a continuous mechanical separator. In one version, the medium filter 108 can have a filter size of approximately 100 microns. Other versions of the medium filter 108 can comprise a filter size range of about 100 microns to about 220 microns, or of about 120 microns to about 190 microns.

Like some of the other filters, the fine filter 109 can be an automatic self-cleaning mechanical filter with a filter size of, for example, approximately 15 microns, or in a filter size range of about 15 to about 140 microns, or about 15 microns to about 120 microns. The fine filter 109 can remove the concentrated trichomes 115 from the remaining liquid. The filtered liquid 117 can be ported to the spray bar 111 at the coarse filter 101, sent back to the holding tank 105 for reuse, and/or sent to final waste. Alternatively, one or more of the filters of the system can be used to selectively collect trichomes in specific ranges of sizes. For example, the system can selectively collect trichomes in a range of about 15 to about 45 microns, about 45 to about 70 microns, about 45 to about 90 microns, or about 70 to about 120 microns, to name a few samples.

In an alternate embodiment, one or more of the first pump 102, liquid ring pump 117, shear blender 103 and coarse filter 101 may be replaced with a tumbling mechanism, such as a continuous tumbling mechanism. This design can allow the biomass to collide with itself, resulting in shear forces that are developed from gravity and rotational speeds. The tumbling mechanism, such as an internally fed drum screen, can introduce biomass to a portion of the filter screen while the biomass travels through the drum. The biomass crashing into itself can remove trichomes from the surfaces of the biomass. The drum, which can comprise wedge wire, perforated, or mesh screen, can simultaneously act as a filter, allowing trichomes to pass through the drum. The biomass can go through the entirety of the drum length while trichomes pass through the drum wall.

In some embodiments, the spray bar 111 can use fluid to physically push the trichomes through the drum wall to (1) keep the drum screen from blinding off, and (2) physically shearing the trichomes from the biomass. The term "physically shearing" can be a stand-alone function of the spray bar 111, in addition to keeping the drum screen from blinding off. One or more of the filters, such as the medium filter 108 and fine filter 109, can be employed downstream to complete the process. Any of the filters can include an internal spinning brush to facilitate filtering. Alternate embodiments can include sieves or strainers, such as sieve bags, instead of filters.

In still another embodiment, the in-line turbulence (or turbulent processor) of the system can be provided by one, two or more pumps without the shear mixer. Such a system also can include a liquid ring pump, such as downstream of the pumps, as described herein.

Figure 2:
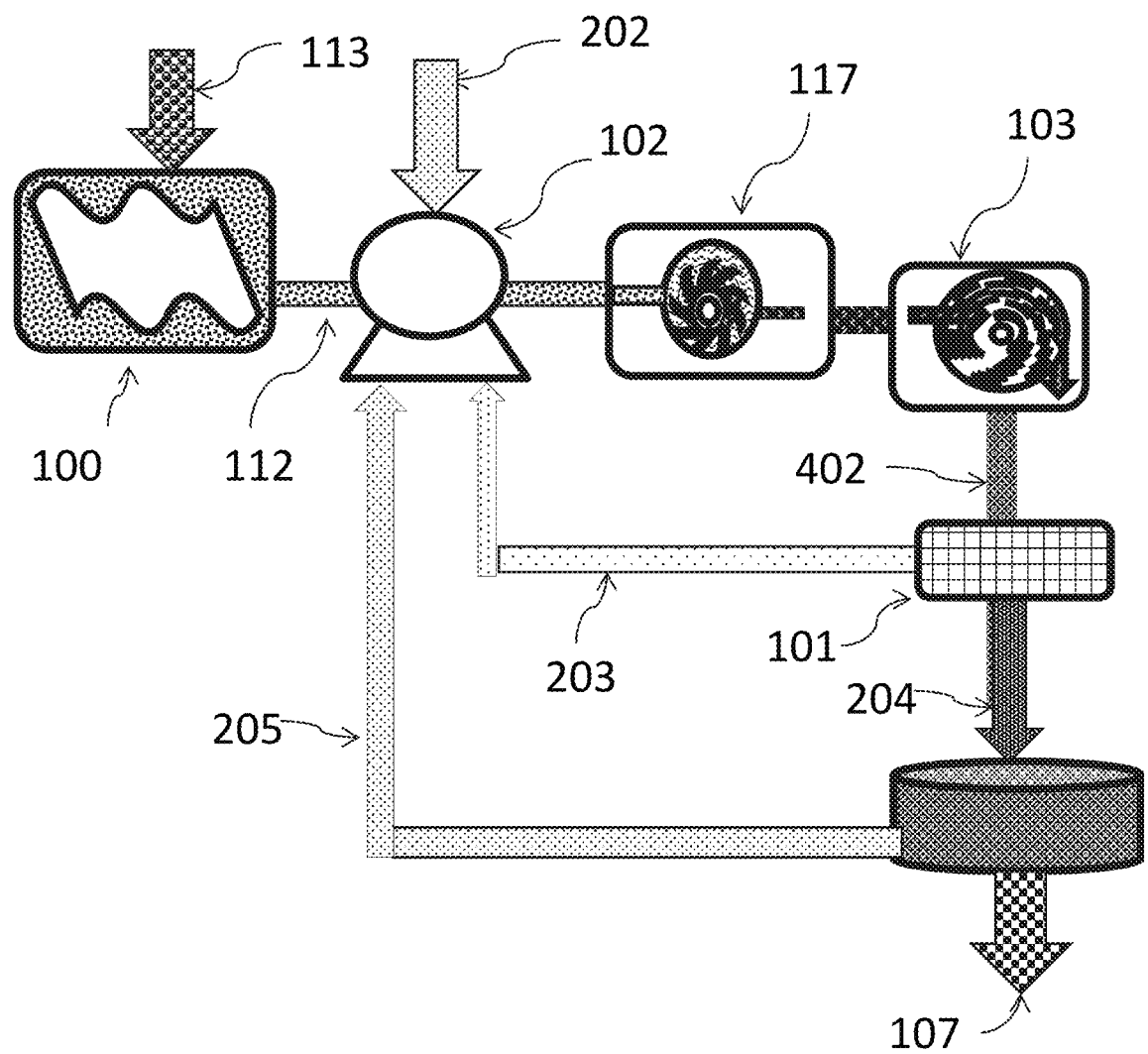
FIG. 2 is a schematic diagram of an embodiment of the equipment for an alternate process when using another solvent as the fluid.

In another alternate embodiment, one or more other solvents may be used instead of water. Embodiments of the downstream equipment and processing can be adjusted as shown, for example, in the schematic FIG. 2. Although embodiments can comprise the same processing steps as described herein, the results of using another solvent can be an extraction of the cannabinoids, rather than merely a separation of the trichomes from the biomass material. Other modifications to the equipment selection can be included, and some examples are described herein. In some cases, the feed device 100 can be a single stage auger feed system that can feed the hopper of the first pump 102. Versions of the first pump 102 can be a progressive cavity pump.

An example of the hopper on the first pump 102 can include paddles that can stir the biomass, and a flanged injection pipe where additional solvent 202 can be injected into the hopper. The slurry 112 can enter the pump 102 as a mixture of bulk cannabis material 113 and the solvent 202. The solvent 202 can include ethanol (e.g., ethyl alcohol), but other suitable liquid solvents and/or additives may be used. The smaller solids effluent 402 from the shear blender(s) 103 can include a cannabinoid tincture mixed with biomass. The smaller solids effluent 402 is fed into the coarse filter 101, that can be a drum screen that separates grade a tincture 203 from the biomass. The grade a tincture 203 is then fed back to the pump 102 for continued processing until the solvent is fully saturated. The remaining biomass 204 is fed into a separator to remove as much liquid as possible, producing a grade b tincture 205 that can also be ported back to the pump 102. Examples of the separator can be a centrifuge device, but may also be a screw press or any other suitable machine that can separate the elements.

The present disclosure addresses the issues of conventional equipment by providing a faster system, apparatus and process that can use one or more of turbulent hydrodynamic, gravitational or rotational shear forces to separate the cannabinoids from the plant material. The process can be used with a liquid, such as water, which can produce a mechanical separation of the trichomes. Water can be used in the context of mechanical separation (e.g., to make "water hash") since cannabinoids may not be readily soluble in water.

Alternatively, another solvent can be used to dissolve the cannabinoids (e.g., CBD and THC molecules, and other high value cannabinoids) out of the trichomes to form a cannabinoid-rich tincture, rather than just separate the trichomes from the biomass.

The process can be automated for continuous, in-line flow production for water, solvent or both. In some versions, yields of desired recovery can be 75% or more, and the system can process 200 to 1000 pounds of plant material or more per hour (e.g., 500 pounds or more). In addition, the system, method and apparatus can be used as a separation or extraction process for any type of plant matter or material. Embodiments of a system, method and apparatus can separate cannabinoids from plants using the turbulent hydrodynamic, gravitational and/or rotational speed shear forces of one or more pumps coupled with one or more shear blenders, or an in-line, continuous drum screen, to separate the cannabinoids from the leaves, flowers, and stems. Milled or ground plant parts can be mixed with liquid to create a slurry mixture that is pumped into a liquid ring or other type of pump. The hydrodynamic turbulence within the liquid ring pump can force cannabinoids from the external surfaces of the plant material to create a mixture of cannabinoids, liquid and large plant material containing more cannabinoids.

In some embodiments, the mixture from the liquid ring pump can be transferred to a shear blender. The rotor-stator clearances within the shear blender can be configured to break apart the botanical material of the cannabis, but are not small enough to impact the trichome structures since they are orders of magnitude smaller than the leaves, flowers and stems of the plant. As the mixture is processed within the shear blender, the plant parts can be further broken down into smaller pieces to expose even more of the cannabinoids. The turbulence within the shear blender can cause the additionally exposed cannabinoids to separate from the plant material. The mixture from the shear blender may be processed through one or more additional shear blenders for additional product maceration and separation. The mixture of the final shear blender can be fed into a filtration system starting with a coarse filter. A positive displacement pump can be used to pull the mixture from the course filter and send it through one or more filters. In other embodiments, the pumps and blenders can be replaced with a drum screen that uses gravitational and/or rotational speed shear forces to separate the trichomes from the biomass. The larger plant material that is filtered out in the first filtration step can be routed back into the system for continued processing. The liquid that is filtered out in the final polishing filtration step can also be routed back into the system for reuse, in some versions.

If a solvent, such as ethanol, is used as the liquid, the cannabinoids can be dissolved during the process such that the mixture from the shear blender is a cannabinoid tincture. The tincture can then be further processed using a centrifuge and/or screw press to separate the remaining tincture from the biomass. In some examples, the process can form an extraction rather than a mere separation. The entire system can be operated continuously or in a batch process.

Other embodiments can include one or more of the following items.

1. A process for separating trichomes from plant material, the process comprising:
   mixing plant material with a fluid in a metered feed system and forming a slurry;
   pumping the slurry into a turbulent processor, agitating the slurry between rotating and static teeth and shearing trichomes from the plant material to form a mixture of fluid, trichomes and plant material;
   coarse filtering the mixture and removing portions of the plant material to form an interim mixture; and then
   second filtering the interim mixture and removing other plant material and some trichomes to form a resulting mixture comprising other trichomes and fluid.

2. The process of item 1, wherein the turbulent processor comprises at least one of a shear blender, liquid ring pump, in-line turbulent mixer, solids handling pump or particle reducer.

3. The process of item 1, further comprising grinding the slurry to reduce a size of the plant material prior to processing in the turbulent processor.

4. The process of item 2, further comprising at least one additional shear blender coupled between the shear blender and the coarse filter and processing the mixture through the additional shear blender prior to coarse filtering.

5. The process of item 1, further comprising at least one medium filter having a filter size and position between the coarse filtering and the second filtering, and filtering the interim mixture with the medium filter prior to pumping the resulting mixture through the second filter.

6. The process of item 1, further comprising a liquid spray system comprising an additional fluid and moving the mixture through the coarse filter with the additional fluid.

7. The process of item 1, wherein pumping the slurry comprises first pumping the slurry through at least one shear blender.

8. The process of item 1, wherein the resultant mixture comprises substantially only discharge fluid.

9. A process for extracting cannabinoids from plant material, the process comprising:
   mixing plant material with a solvent in a hopper and forming a slurry;
   pumping the slurry into a turbulent processor, agitating the slurry and extracting cannabinoids from the plant material and forming a mixture of solvent with plant material and dissolved cannabinoids;
   coarse filtering the mixture and removing portions of the plant material to form an interim mixture of solvent, other plant material and dissolved cannabinoids;
   second filtering the interim mixture and removing the other plant material to form a resulting solution comprising substantially only the solvent and dissolved cannabinoids; and then
   processing the resulting solution to remove the dissolved cannabinoids from the solvent.

10. The process of item 9, further comprising at least one shear blender or liquid ring pump and processing the mixture prior to coarse filtering.

11. A system for separating trichomes from plant material, the system comprising:
    a metered feed system configured to mix plant material with a fluid to form a slurry;
    a turbulent processor comprising a shear blender and configured to receive and agitate the slurry between rotating and static teeth and shear trichomes from the plant material to form a mixture of fluid, trichomes and plant material;
    a coarse filter configured to remove some plant material from the mixture to form an interim mixture; and
    a second filter is configured to remove other plant material from the interim mixture and form a resultant mixture comprising fluid and trichomes.

12. The system of item 11, wherein the turbulent processor comprises at least one of a liquid ring pump, an in-line turbulent mixer, a solids handling pump or a particle reducer.

13. The system of item 11, further comprising a grinder configured to grind the slurry to reduce a size of the plant material prior to processing in the turbulent processor.

14. The system of item 11, further comprising at least one additional shear blender configured to be coupled between the shear blender and the coarse filter and configured to process the mixture through the additional shear blender prior to coarse filtering.

15. The system of item 11, further comprising at least one medium filter having a filter size and position between the coarse filtering and the second filtering, and configured to filter the resulting mixture with the medium filter prior to pumping the interim mixture through the second filter.

16. The system of item 11, further comprising a liquid spray system configured to comprise an additional fluid and configured to move the mixture through the coarse filter with the additional fluid.

17. The system of item 11, wherein the turbulent processor comprises a pump configured to be located upstream from the shear blender.

18. A system for extracting cannabinoids from plant material, the system comprising:
    a hopper configured to mix plant material with a solvent to form a slurry;
    a turbulent processor configured to receive and agitate the slurry to extract cannabinoids from the plant material to form a mixture of solvent, plant material and dissolved cannabinoids;
    a coarse filter configured to remove some portions of the plant material from the mixture to form an interim mixture of solvent, other plant material and dissolved cannabinoids;
    a second filter configured to remove other portions of the plant material from the interim mixture to form a solution comprising substantially only the solvent and dissolved cannabinoids; and
    equipment configured to process the mixture to remove the dissolved cannabinoids from the solvent.

19. The system of item 18, further comprising at least one pump or shear blender configured to be coupled upstream from the coarse filter and configured to process the mixture prior to coarse filtering.

20. The system of item 18, wherein the solvent is configured to comprise ethanol and at least one additive, such as water (e.g., from the ambient air) or other co-solvents.

This written description uses examples to disclose the embodiments, including the best mode, and also to enable those of ordinary skill in the art to make and use the invention. The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

Note that not all of the activities described above in the general description or the examples are required, that a portion of a specific activity may not be required, and that one or more further activities can be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

It can be advantageous to set forth definitions of certain words and phrases used throughout this patent document. The term "communicate," as well as derivatives thereof, encompasses both direct and indirect communication. The term "discreet," as well as derivatives thereof, references to the amount of skin exposed by a user of the garment, rather than the type of style of the garment. The terms "include" and "comprise," as well as derivatives thereof, mean inclusion without limitation. The term "or" is inclusive, meaning and/or. The phrase "associated with," as well as derivatives thereof, can mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items can be used, and only one item in the list can be needed. For example, "at least one of: A, B, and C" includes any of the following combinations: A, B, C, A and B, A and C, B and C, and A and B and C.

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function.

Benefits, other advantages, and solutions to problems have been described above with regard to specific embodiments. However, the benefits, advantages, solutions to problems, and any feature(s) that can cause any benefit, advantage, or solution to occur or become more pronounced are not to be construed as a critical, required, sacrosanct or an essential feature of any or all the claims.

After reading the specification, skilled artisans will appreciate that certain features are, for clarity, described herein in the context of separate embodiments, can also be provided in combination in a single embodiment. Conversely, various features that are, for brevity, described in the context of a single embodiment, can also be provided separately or in any subcombination. Further, references to values stated in ranges include each and every value within that range.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. As used herein, the terms "substantial" and "substantially" means, when comparing various parts to one another, that the parts being compared are equal to or are so close enough in dimension that one skill in the art would consider the same. Substantial and substantially, as used herein, are not limited to a single dimension and specifically include a range of values for those parts being compared. The range of values, both above and below (e.g., "+/−" or greater/lesser or larger/smaller), includes a variance that one skilled in the art would know to be a reasonable tolerance for the parts mentioned.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A system for separating trichomes from plant material, the system comprising:
   a metered feed system configured to mix the plant material with a fluid to form a slurry;
   a turbulent processor comprising a shear blender and configured to receive and agitate the slurry between rotating and static teeth and shear the trichomes from the plant material to form a mixture of the fluid, the trichomes and the plant material;
   a coarse filter configured to remove some of the plant material from the mixture to form an interim mixture; and
   a second filter is configured to remove other plant material from the interim mixture and form a resultant mixture comprising the fluid and the trichomes.

2. The system of claim 1, wherein the turbulent processor further comprises at least one of a liquid ring pump or a sinusoidal pump.

3. The system of claim 1, further comprising a grinder configured to grind the slurry to reduce a size of the plant material prior to processing in the turbulent processor.

4. The system of claim 1, further comprising at least one additional shear blender configured to be coupled between the shear blender and the coarse filter and configured to process the mixture through the at least one additional shear blender prior to coarse filtering.

5. The system of claim 1, further comprising at least one medium filter having a filter size and position between the coarse filtering and the second filtering, and configured to filter the interim mixture with the at least one medium filter prior to pumping the interim mixture through the second filter.

6. The system of claim 1, further comprising a liquid spray system configured to comprise an additional fluid and configured to move the mixture through the coarse filter with the additional fluid.

7. The system of claim 2, wherein the turbulent processor further comprises a first pump configured to be located upstream from the at least one of the liquid ring pump or the sinusoidal pump.

8. A system for extracting cannabinoids from plant material, the system comprising:
 a hopper configured to mix the plant material with a solvent to form a slurry;
 a turbulent processor configured to receive and agitate the slurry to extract cannabinoids from the plant material to form a mixture of the solvent, the plant material and dissolved cannabinoids;
 a coarse filter configured to remove some portions of the plant material from the mixture to form an interim mixture of the solvent, other plant material and the dissolved cannabinoids;
 a second filter configured to remove other portions of the plant material from the some portions of the plant material to form a solution comprising substantially only the solvent and the dissolved cannabinoids; and
 equipment configured to process the mixture to remove the dissolved cannabinoids from the solvent.

9. The system of claim 8, further comprising at least one additional shear blender configured to be coupled upstream from the coarse filter and configured to process the mixture prior to coarse filtering.

10. The system of claim 8, wherein the solvent is configured to comprise ethanol and at least one additive.

11. The system of claim 1, wherein the rotating and static teeth define a prescribed clearance therebetween configured to allow the trichomes to pass through without damage.

12. The system of claim 11, wherein the prescribed clearance is in a range of approximately 0.1 millimeters to approximately 1 millimeter.

13. The system of claim 2, wherein liquid ring pump includes a turbulent internal mechanism configured to remove the trichomes from the plant material in addition to moving the slurry, the turbulent internal mechanism including a spinning off-center blade ring rotatable within a ring configured to pull the slurry and circulate the slurry as a high solids mixture including the trichomes.

14. The system of claim 2, wherein the sinusoidal pump includes an inlet receiving the slurry into a housing containing a sinusoidal rotor rotated on a shaft to define four evenly-sized chambers, the sinusoidal pump is configured to pull the slurry into each chamber in sequence before discharging a high solids mixture from an outlet of the housing.

15. The system of claim 1, further including a diaphragm valve disposed downstream of the shear blender to create backpressure to slow the mixture of the fluid, the trichomes and the plant material through the shear blender.

16. The system of claim 1, further including pipes from at least one of the coarse filter and the second filter to the metered feed system for routing at least one of the interim mixture from the coarse filter and the resultant mixture from the second filter back to the metered feed system for continued processing and reuse.

17. The system of claim 8, wherein the turbulent processor comprises a shear blender including rotating and static teeth configured to receive and agitate the slurry and shear trichomes from the plant material to form the mixture of the solvent, the plant material and dissolved cannabinoids, the rotating and static teeth defining a prescribed clearance therebetween configured to allow the trichomes to pass through without damage.

18. The system of claim 8, further including a first pump coupled upstream from the coarse filter and configured to process the mixture prior to coarse filtering and wherein the second filter comprises a separator and the interim mixture from the coarse filter comprises a grade a tincture and the solution comprising substantially only the solvent and the dissolved cannabinoids comprises a grade b tincture.

19. A system for separating trichomes from plant material, the system comprising:
 a metered feed system configured to mix the plant material with a fluid to form a slurry;
 at least one shear blender configured to receive and agitate the slurry between rotating and static teeth and shear the trichomes from the plant material to form a mixture of the fluid, the trichomes and the plant material;
 a liquid ring pump disposed upstream from the at least one shear blender and downstream from the metered feed system and configured to remove the trichomes from the plant material in addition to moving the slurry, the liquid ring pump including a spinning off-center blade ring rotatable within a ring configured to pull the slurry and circulate the slurry as a high solids mixture including the trichomes;
 a coarse filter configured to remove some of the plant material from the mixture to form an interim mixture; and
 a second filter is configured to remove other plant material from the interim mixture and form a resultant mixture comprising the fluid and the trichomes.

* * * * *